United States Patent [19]

Oeser et al.

[11] 4,229,365

[45] Oct. 21, 1980

[54] MANUFACTURE OF SUBSTITUTED FLUOROBENZENES

[75] Inventors: Heinz-Guenter Oeser, Ludwigshafen; Karl-Heinz Koenig, Frankenthal; Dietrich Mangold, Neckargemuend, all of Fed. Rep. of Germany

[73] Assignee: BASF Aktiengesellschaft, Fed. Rep. of Germany

[21] Appl. No.: 907,912

[22] Filed: May 22, 1978

[30] Foreign Application Priority Data

May 28, 1977 [DE] Fed. Rep. of Germany ....... 2724366
May 28, 1977 [DE] Fed. Rep. of Germany ....... 2724367

[51] Int. Cl.$^2$ .................... C07C 121/52; C07C 79/12
[52] U.S. Cl. ................ 260/465 G; 568/588; 568/937; 568/938
[58] Field of Search .................. 260/465 G, 646; 568/588

[56] References Cited

U.S. PATENT DOCUMENTS

| | | | |
|---|---|---|---|
| 3,064,058 | 11/1962 | Duesel et al. ........................ | 260/646 |
| 3,240,824 | 3/1966 | Boudakian et al. .................. | 260/646 |
| 4,069,262 | 1/1978 | Kunz ................................... | 260/646 |

OTHER PUBLICATIONS

Finger et al., J. Am. Chem. Soc., vol. 78 (1956), pp. 6034 to 6036.
Starr et al., Chemistry and Industry, 1962, pp. 1328 to 1329.
Vorozhtsov et al., Chem. Abstracts, vol. 57 (1962) 9706h to 9707h.
Matsui et al., Chem. Abstracts, vol. 82, 155717f (1975).

*Primary Examiner*—Leland A. Sebastian
*Attorney, Agent, or Firm*—Keil & Witherspoon

[57] ABSTRACT

Fluorobenzenes are manufactured by reacting substituted chlorobenzenes with potassium fluoride in the presence of catalytic amounts of cesium fluoride and in the presence of certain solvents; m-nitrofluorobenzenes and m-cyanofluorobenzenes can also be manufactured in the absence of cesium fluoride. The products are starting materials for the manufacture of dyes, pharmaceuticals and pesticides.

9 Claims, No Drawings

MANUFACTURE OF SUBSTITUTED FLUOROBENZENES

The present invention relates to a novel process for the manufacture of a substituted fluorobenzene by reacting a substituted chlorobenzene with potassium fluoride in the presence of a catalytic amount of cesium fluoride and in the presence of certain solvents; the manufacture of m-nitrofluorobenzenes and m-cyanofluorobenzenes can also be carried out in the absence of cesium fluoride.

Chemistry and Industry 1962, pages 1,328 and 1,329, discloses the manufacture of o- and p-fluoronitrobenzene by reacting the corresponding chlorobenzene with potassium fluoride at from 221 to 230° C. for 7 hours; dimethylsulfone is used as the solvent and the yield is from 60 to 73 percent. It is pointed out that in dimethylformamide and dimethylsulfoxide the fluorination in most cases only takes place sluggishly and the conversion is unsatisfactory. In dimethylsulfoxide, the reaction mixture undergoes some decomposition, with the formation of evil-smelling, sulfur-containing by-products; reaction times of 15 hours are specified.

J. Amer. Chem. Soc., 78 (1956), 6,034-6,036 discloses the conversion of various mononitrochlorobenzenes in dimethylformamide and dimethylsulfoxide at from 175° to 190° C., with reaction times of from 2 to 163 hours and yields of from 10 to 72 percent. The conversion of 2-chloronitrobenzene in dimethylformamide gives an estimated yield of only 40 percent in spite of being carried out for 163 hours at 170° C.

Chemical Abstracts, 57 (1962), 9,706 h to 9,707 b discloses that instead of using potassium fluoride, the reaction can be carried out with cesium fluoride at from 190° to 200° C. in the absence of a solvent, and with a reaction time of 25 hours; an excess of from 30 to 50 percent of cesium fluoride over the stoichiometric amount is necessary. o-Fluoronitrobenzene is obtained in a yield of from 8 to 80 percent whilst the p-isomer is obtained in a yield of from 70 to 80 percent.

U.S. Pat. No. 3,064,058 discloses a similar reaction in tetramethylenesulfone as the solvent. In order to obtain a dry reaction mixture, the process is carried out by first suspending the alkali metal fluoride in the solvent and then distilling the suspension until all the water present in the suspension has been removed together with from 5 to 15 percent by weight of tetramethylenesulfone. p-Nitrochlorobenzene is then added to the suspension. Only sodium fluoride and potassium fluoride are mentioned as alkali metal fluorides, and the Examples refer only to potassium fluoride. As shown by the Examples, a yield of 93.5 percent is achieved with a reaction temperature of 240° C. and a reaction time of 12 hours, to which must be added the time required for the distillation.

U.S. Pat. No. 3,240,824 concludes, from the above prior art, that mononitro-o-chlorobenzenes and mononitro-p-chlorobenzenes can best be reacted with potassium fluoride as the sole alkali metal fluoride, in the absence of a solvent, at from 270° to 320° C. It points out that the use of cesium fluoride is too uneconomical and that if a solvent is used it requires an involved method of recovery entailing losses; drying the solvent-containing starting mixture is frequently difficult and requires a special fractionation technique. Taking all the Examples into account, the conditions proposed in the U.S. Patent give, with reaction times of 24 hours, yields of only 56.5 percent (o-compound) or 60.6 percent (p-compound), and conversions of 50.5 percent (o-compound) or 52.5 percent (p-compound).

All the publications relate only to conversion of p- or o-chloronitrobenzenes; hitherto, it has not been possible to manufacture the m-fluoro compound directly in one step from the m-chloro compound. Hence it has been necessary to manufacture m-nitrofluorobenzenes in an involved manner by diazotizing the corresponding m-nitroanilines using fluoboric acid and then thermally decomposing the diazonium tetrafluoborates (Berichte der Deutschen Chemischen Gesellschaft, 62, 3,041). The m-cyanofluorobenzenes were subsequently obtainable by reducing the m-nitrofluorobenzenes to the corresponding anilines and then subjecting these to the Sandmeyer reaction (J. Chim. Phys., 20, 74).

We have found that a substituted fluorobenzene of the formula

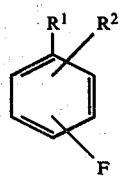

I where $R^1$ is nitro or cyano and $R^2$ is hydrogen, an aliphatic radical or halogen, is obtained in an advantageous manner by reacting a substituted chlorobenzene with potassium fluoride in the presence of a solvent, if the chlorobenzene of the formula

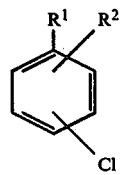

II where $R^1$ and $R^2$ have the above meanings is reacted (with potassium fluoride) in the presence of a catalytic amount of cesium fluoride or, if the starting material II is a m-nitrochlorobenzene or m-cyano-chlorobenzene, also in the absence of cesium fluoride, and in the presence of a N,N-disubstituted carboxylic acid amide, nitrobenzene, nitrile, aliphatic sulfone and/or aliphatic sulfoxide as the solvent.

If o-chloronitrobenzene is used, the reaction may be represented by the following equation:

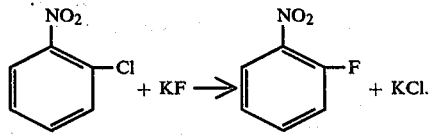

Compared to the prior art, the process of the invention, applied to the manufacture of fluorobenzenes, gives excellent results in respect of yield, purity of the end product, low reaction temperature and short reaction time. The yield and purity are better than in virtually any other process. Compared to the process disclosed in Chemical Abstracts, 57 (loc. cit.), the reaction time is substantially shorter and the process is more economical and can also be carried out on an individual scale. Compared to the process disclosed in U.S. Pat. No. 3,064,058, simple drying of the potassium fluoride, for example for from 1.5 to 2.5 hours in a drying oven, suffices, and the involved azeotropic removal of water can be dispensed with, thereby eliminating losses in operating time, solvent and energy. All these advantageous results are surprising in view of the prior art.

Compared to the prior art, the invention provides m-nitrofluorobenzenes and m-cyanofluorobenzenes by a simpler and more economical method. Compared to the conventional processes, the fact that the synthesis is carried out in one step results in a substantially shorter operating time and more economical operation, especially on an industrial scale.

The starting material II is reacted with potassium fluoride, generally in the stoichiometric amount or with the latter in excess, preferably with from 1 to 5, especially from 2 to 4.5, moles of potassium fluoride per mole of starting material II. Preferred starting materials II and accordingly preferred end products I are those where $R^1$ is nitro or cyano and $R^2$ is hydrogen or alkyl of 1 to 8 carbon atoms, which may be substituted by groups which are inert under the reaction conditions, e.g. alkoxy of 1 to 4 carbon atoms, or is bromine, iodine or especially fluorine. The fluorine of the end product I or the chlorine of the starting material II may be in the meta-position, advantageously in the para-position and especially in the ortho-position to the nitro group or cyano group and, in the case of an m-chlorobenzene, gives the end products of the formula

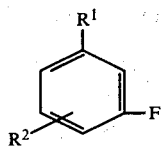

where $R^1$ is nitro or cyano and $R^2$ is hydrogen, an aliphatic radical or halogen.

Examples of suitable substituted chlorobenzenes II are o-chloronitrobenzene, m-chloronitrobenzene, p-chloronitrobenzene, o-chlorobenzonitrile, m-chlorobenzonitrile and p-chlorobenzonitrile; 2-methyl-, 2-ethyl-, 2-propyl-, 2-isopropyl-, 2-butyl-, 2-isobutyl-, 2-sec.-butyl-, 2-tert.-butyl- and 2-fluoro-4-chloronitrobenzene and corresponding 3-substituted 4-chloronitrobenzenes; 4-methyl-, 4-ethyl-, 4-propyl, 4-isopropyl-, 4-butyl-, 4-isobutyl-, 4-sec.-butyl-, 4-tert.-butyl- and 4-fluoro-2-chloronitrobenzene and corresponding 2-chloro-nitro-benzenes substituted in the 3-position, 5-position or 6-position instead of in the 4-position; correspondingly substituted 2-chlorobenzonitriles and 4-chlorobenzonitriles, and 2-methyl-, 2-ethyl-, 2-propyl-, 2-isopropyl-, 2-butyl-, 2-isobutyl-, 2-sec.-butyl-, 2-tert.- butyl- and 2-fluoro-3-chloro-nitrobenzene; 4-methyl-, 4-ethyl-, 4-propyl-, 4-isopropyl-, 4-butyl-, 4-isobutyl-, 4-sec.-butyl-, 4-tert.-butyl and 4-fluoro-3-chloro-nitrobenzene and corresponding 3-chloro-nitrobenzenes substituted in the 5-position or 6-position instead of in the 4-position; and correspondingly substituted 3-chlorobenzonitriles.

The catalyst which is used for o- and p-nitrochlorobenzenes and -cyanochlorobenzenes, and may or may not be used for the m-compounds, is cesium fluoride, which is advantageously employed in an amount of not more than 0.1 mole, advantageously from 0.001 to 0.1 mole, preferably from 0.003 to 0.03 mole, and especially from 0.05 to 0.025 mole per mole of starting material II. Examples of suitable solvents are N,N-disubstituted carboxamides, e.g. dimethylformamide and tetramethylurea; nitrobenzene; and nitriles, e.g. acetonitrile and benzonitrile; preferred solvents are dimethylformamide and especially aliphatic sulfones and sulfoxides, advantageously of the formula

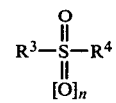

where $R^3$ and $R^4$ are identical or different and each is an aliphatic radical, preferably alkyl of 1 to 8 carbon atoms, especially of 1 to 4 carbon atoms, or $R^3$ and $R^4$ together are alkylene of 4 or 5 carbon atoms, and n is 0 or 1. Examples of suitable solvents III are dimethylsulfoxide, diethylsulfoxide, dipropylsulfoxide, diisopropylsulfoxide, di-n-butylsulfoxide, diisobutylsulfoxide, dipentylsulfoxide, dihexylsulfoxide, diheptylsulfoxide, dioctylsulfoxide, methylethylsulfoxide, tetramethylenesulfoxide, pentamethylenesulfoxide, dimethylsulfone, diethylsulfone, dipropylsulfone, diisopropylsulfone, dibutylsulfone, diisobutylsulfone, dipentylsulfone, dihexylsulfone, diheptylsulfone, dioctylsulfone, methylethylsulfone, tetramethylenesulfone and pentamethylenesulfone; tetramethylenesulfone is particularly preferred. Solvent mixtures may also be used. The solvent is advantageously used in an amount of from 50 to 1,000 percent by weight, preferably from 100 to 200 percent by weight, based on starting material II.

The reaction is in general carried out at from 150° to 250° C., advantageously from 150° to 240° C., especially from 160° to 238° C., preferably from 200° to 235° C., under atmospheric or superatmospheric pressure, continuously or batchwise. In the case of the reaction of an m-monochlorobenzene II, a reaction temperature of from 200° to 250° C., advantageously from 200° to 240° C., more particularly from 200° to 238° C. and especially from 210° to 235° C., is preferred.

The reaction may be carried out as follows: a mixture of starting material II, potassium fluoride, cesium fluoride and solvent or, in the case of a m-nitrochlorobenzene or a m-cyanochlorobenzene, a mixture of starting material II, potassium fluoride and solvent, is kept at the reaction temperature for from 2 to 100 hours. Before the reaction, the potassium fluoride is dried in any suitable manner, advantageously by a method which is simple to operate, for example in a drying chamber or chamber dryer, ribbon dryer or rack dryer; however, fluidized bed dryers, drum dryers and disk dryers may also be used. After the reaction, the end product is isolated in the conventional manner, for example by filtering the mixture, washing the solid residue and distilling the filtrate and wash filtrates.

The substituted fluorobenzenes obtainable by the process of the invention are valuable starting materials for the manufacture of dyes, pharmaceuticals and pesticides. For example, they can be reduced to fluoroanilines which are employed in paints, germicides and solder fluxes. Regarding their use, reference may be made to the above publications.

In the Examples which follow, parts are by weight.

EXAMPLE 1

(a) 1,300 parts of o-chloronitrobenzene, 960 parts of potassium fluoride and 25 parts of cesium fluoride are stirred in 1,300 parts of tetramethylenesulfone under nitrogen for 16 hours at 225° C. The solution is cooled to 110° C. and filtered, the solid residue is washed with 500 parts of methylene chloride and the filtrates are combined and distilled. 991 parts (85.5% of theory) of o-fluoronitrobenzene of boiling point 55° to 57° C/1.2 mm Hg are obtained.

(b) Comparative experiment: the reaction is carried out as described in Example 1(a), but without cesium fluoride. 348 parts (30% of theory) of o-fluoronitrobenzene of boiling point 55°–57° C./1.2 mm Hg are obtained.

EXAMPLE 2

1,500 parts of 3,4-dichloronitrobenzene, 680 parts of potassium fluoride and 5 parts of cesium fluoride are stirred in 1,500 parts of tetramethylenesulfone under nitrogen for 3 hours at 220° C. Working up takes place as described in Example 1(a). 1,275 parts (93% of theory) of 3-chloro-4-fluoronitrobenzene of melting point 41°–42° C. are obtained.

EXAMPLE 3

(a) A suspension of 1,500 parts of 3,4-dichloronitrobenzene, 900 parts of potassium fluoride and 10 parts of cesium fluoride in 800 parts of dimethylformamide is refluxed for 16 hours (165° C.). The mixture is worked up as described in Example 1(a). 1,110 parts (81% of theory) of 3-chloro-4-fluoronitrobenzene of melting point 41°–42° C. are obtained.

(b) Comparative experiment: the reaction is carried out as described in Example 1(b), without adding cesium fluoride. After reacting for 25 hours, 1,042 parts (76% of theory) of 3-chloro-4-fluoronitrobenzene of melting point 41°–42° C. are obtained.

EXAMPLE 4

1,500 parts of 3-chloro-4-fluoronitrobenzene, 25 parts of cesium fluoride and 1,000 parts of potassium fluoride are heated in 1,500 parts of tetramethylenesulfone for 16 hours at 230° C. The mixture is worked up as described in Example 1(a). 139 parts (10.3% of theory) of 3,4-difluoronitrobenzene of boiling point 54° C./1 mm Hg are obtained.

EXAMPLE 5

1,500 parts of 3-chloro-4-fluoronitrobenzene and 1,000 parts of potassium fluoride are heated in 1,500 parts of tetramethylenesulfone for 16 hours at 230° C. The solution is cooled to 110° C. and filtered, the solid residue is washed with 500 parts of methylene chloride and the filtrates are combined and distilled. 139 parts (10.3% of theory) of 3,4-difluoronitrobenzene of boiling point 54° C./1 mbar are obtained.

We claim:

1. A process for the manufacture of a substituted fluorobenzene of the formula

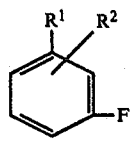

where $R^1$ is nitro or cyano and $R^2$ is hydrogen, an aliphatic radical or halogen, by reacting a substituted chlorobenzene of the formula

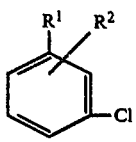

where $R^1$ and $R^2$ have the above meanings, with potassium fluoride in the presence of a solvent and in the presence of from 0.001 to 0.1 mole of cesium fluoride per mole of starting material II, or in the absence of cesium fluoride and in the presence of an N,N-disubstituted carboxylic acid amide, nitrobenzene, nitrile, aliphatic sulfone and/or aliphatic sulfoxide as the solvent.

2. A process as claimed in claim 1, wherein the reaction is carried out with from 1 to 5 moles of potassium fluoride per mole of starting material II.

3. A process as claimed in claim 1, wherein the reaction is carried out with from 0.003 to 0.03 mole of cesium fluoride per mole of starting material II.

4. A process as claimed in claim 1, wherein the reaction is carried out with tetramethylurea, nitrobenzene, acetonitrile, benzonitrile and/or dimethylformamide as the solvent.

5. A process as claimed in claim 1, wherein the reaction is carried out with an aliphatic sulfone or sulfoxide of the formula

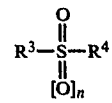

where $R^3$ and $R^4$ are identical or different and each is alkyl of 1 to 8 carbon atoms or $R^3$ and $R^4$ together are alkylene of 4 or 5 carbon atoms, and n is 0 or 1 as the solvent.

6. A process as claimed in claim 1, wherein the reaction is carried out with from 50 to 1,000 percent by weight of solvent, based on starting material II.

7. A process as claimed in claim 1, wherein the reaction is carried out at from 150° to 250° C.

8. A process as claimed in claim 1, wherein starting material II is a m-monochlorobenzene and the reaction is carried out at from 200° to 250° C.

9. A process as defined in claim 1, wherein the reaction is carried out with from 0.05 to 0.025 mole of cesium fluoride per mole of starting material II and at a temperature from 200° to 235° C.

* * * * *